United States Patent [19]

Moorse et al.

[11] Patent Number: 4,662,886

[45] Date of Patent: May 5, 1987

[54] SURGICAL ELEMENT

[75] Inventors: David J. Moorse, Redditch; Angus E. Strover, Belbroughton, both of England

[73] Assignee: A. W. Showell (Surgicraft) Limited, United Kingdom

[21] Appl. No.: 740,960

[22] Filed: Jun. 4, 1985

[30] Foreign Application Priority Data

Jun. 4, 1984 [GB] United Kingdom ............ 8414344

[51] Int. Cl.⁴ .............................................. A61F 2/08
[52] U.S. Cl. .................................... 623/13; 128/335.5; 623/66
[58] Field of Search ............................ 623/13, 16, 66; 128/335.5, 1 R, 334 R

[56] References Cited

U.S. PATENT DOCUMENTS

| 3,130,728 | 4/1964 | Pearson et al. | 128/335.5 |
|---|---|---|---|
| 3,745,590 | 7/1973 | Stubstad | 623/13 |
| 3,805,300 | 4/1974 | Tascon-Alonso et al. | 623/13 |
| 3,987,497 | 10/1976 | Stoy et al. | 623/13 |
| 4,149,277 | 4/1979 | Bokros | 623/16 |
| 4,301,551 | 11/1981 | Dore et al. | 623/13 |
| 4,510,934 | 4/1985 | Batra | 128/335.5 |

FOREIGN PATENT DOCUMENTS

| 51954 | 5/1982 | European Pat. Off. . | |
| 106501 | 4/1984 | European Pat. Off. . | |
| 0169045 | 1/1986 | European Pat. Off. | 623/66 |
| 2949920 | 3/1981 | Fed. Rep. of Germany | 623/66 |
| 0041853 | 9/1983 | Japan | 623/13 |
| 1317417 | 5/1973 | United Kingdom. . | |
| 1602834 | 11/1981 | United Kingdom . | |

Primary Examiner—Richard J. Apley
Assistant Examiner—Alan W. Canon
Attorney, Agent, or Firm—King & Schickli

[57] ABSTRACT

A surgical element (1), such as a suture or a replacement for a ligament, comprises a core (2) consisting of a multiplicity of flexible filaments, such as fine carbon fibres, and partial sheathing (3) formed of standard implantable grade polymer, such as a polyester, in at least two groups (3X, 3Y) totalling less in width than the circumference of the core and interwoven in contra-rotation so that areas (4) of the core are exposed at frequent intervals, to encourage penetration and ingrowth of fresh tissue between the core filaments.

9 Claims, 8 Drawing Figures

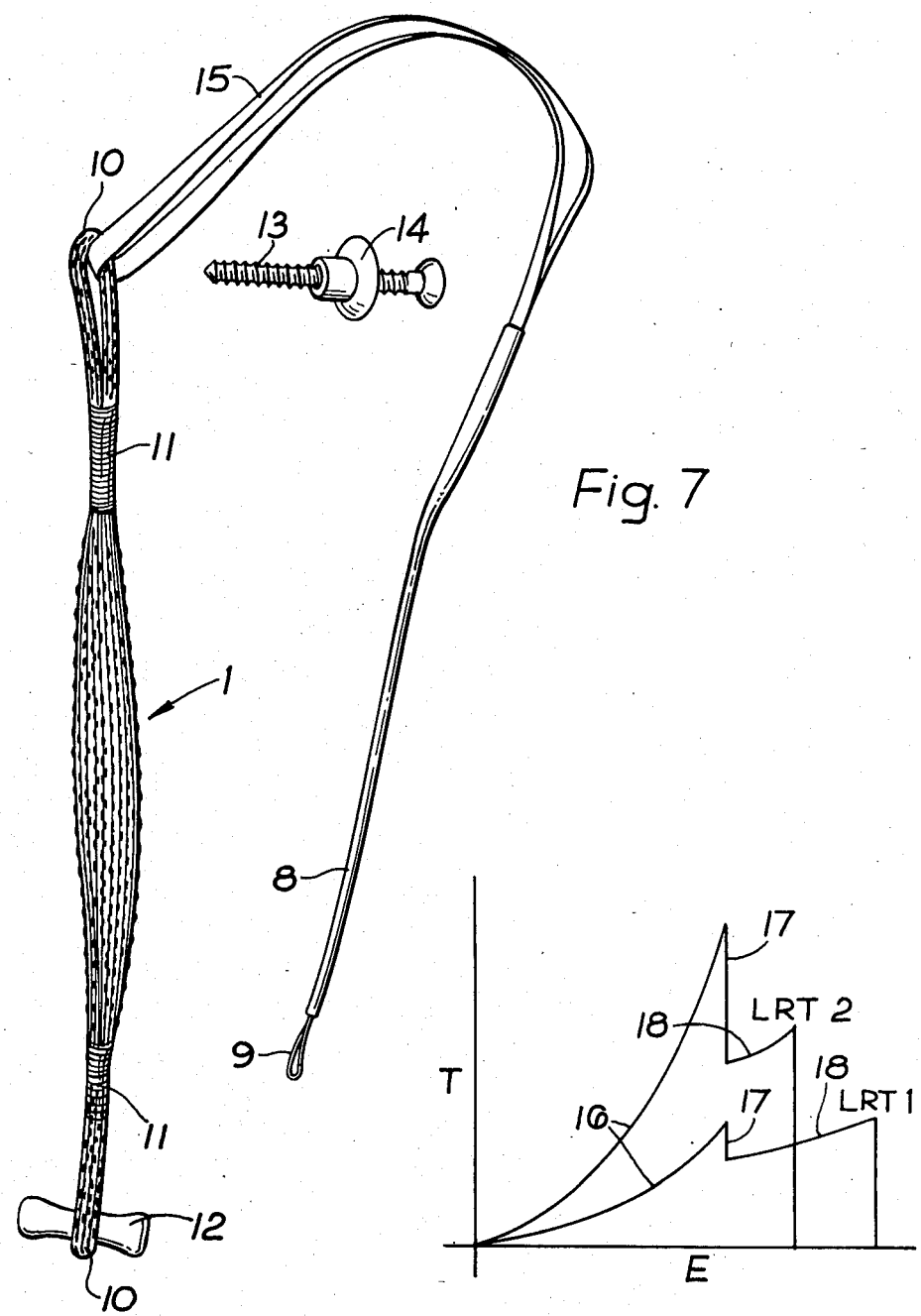

SURGICAL ELEMENT

This invention relates to a surgical element of elongate flexible nature capable of being used singly as a suture or in multiple lengths as a prosthesis or replacement element for a ligament or tendon.

According to the present invention, a surgical element comprises a core consisting of a multiplicity of flexible filaments and partial sheathing therefor formed of filaments of at least one standard implantable grade polymer distributed in at least two groups of a width such that the aggregate of their widths is less than the circumference of the core, the groups of sheathing filaments being interwoven with contra-rotation about the core so that areas of the core filaments are exposed at frequent intervals along the length of the element.

The core filaments may be fine carbon fibres or they may be formed of biocompatible or bioreactive polymer, but—whatever the material of the core filaments—the exposing of areas of core filaments encourages penetration and ingrowth of fresh tissue between the core filaments. The polymer, of both the sheathing filaments and of a core of polymer, may be a polyester.

A method of forming a surgical element in accordance with the invention comprises braiding the sheathing filaments about the core filaments in a braiding machine in which a number of the bobbins are not utilised, and in which at least two sets of contra-rotating bobbins are utilised.

The core filaments may be under negligible tension during the weaving of the sheathing filaments, so that the core filaments in the exposed areas tend to bulge and separate slightly, thus further encouraging penetration and ingrowth of fresh tissue. When the surgical element is placed under tension the sheathing filaments will take the initial strain, until such time that their extension equals the predetermined slack in the core filaments, which will thereafter also take strain.

Thus, with two equal sets of contra-rotating bobbins, two equal groups of sheathing filaments, will be interwoven and the exposed areas of core filaments will alternate from side-to-side of the element, giving a sinusoidal or 'zigzag' appearance to the element.

Surgical elements in accordance with the invention of any length can be cut from a continuous production (or substantially so), and one end of each length may be secured to a needle, for use of the element as a suture, e.g., in a hernia operation, and the other end may be whipped or bonded or sheathed with plastics material to prevent it unravelling.

Alternatively, a length may be doubled up, two or more times, e.g., forty times, to form a prosthesis or replacement element for a ligament or tendon, and a loop (or loops) at one or each end may form an eye (or eyes), for use in securing to bone by means of an attachment device, e.g., a screw or bollard, engaging with the eye. Again the loop (or loops) at one end—or the adjacent ends of a plurality of lengths in accordance with the invention extending side-by-side—may be provided with a probe formed by a plastics sleeve, to assist insertion through a hole in bone, and which probe may thereafter be cut off.

A biocompatible lubricant is preferably applied to the surgical element to ease its passage through tissue and/or bone during the operative procedure.

A number of embodiments of the invention will now be described, by way of example only, with reference to the accompanying drawings, in which.

Figure 2:
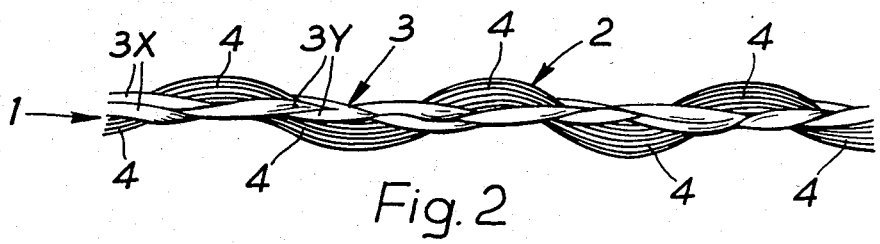
FIG. 2 is an enlargement of a portion 'A', of the surgical element shown in FIG. 1.
Figure 4:
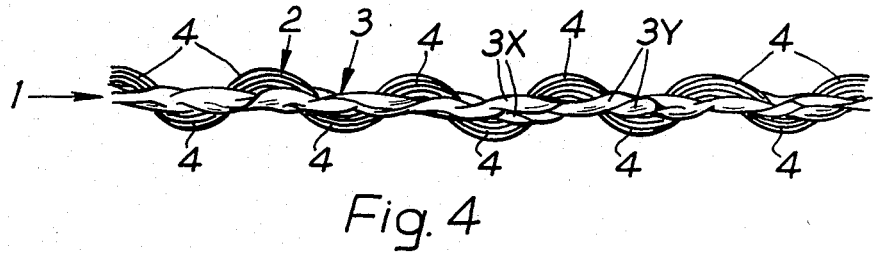
Figure 5:
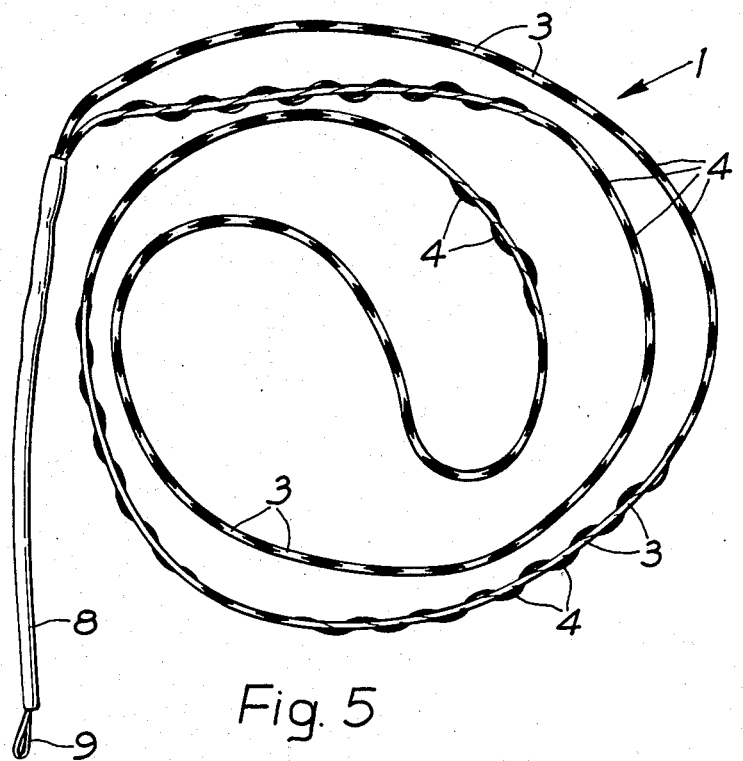
Figure 6:
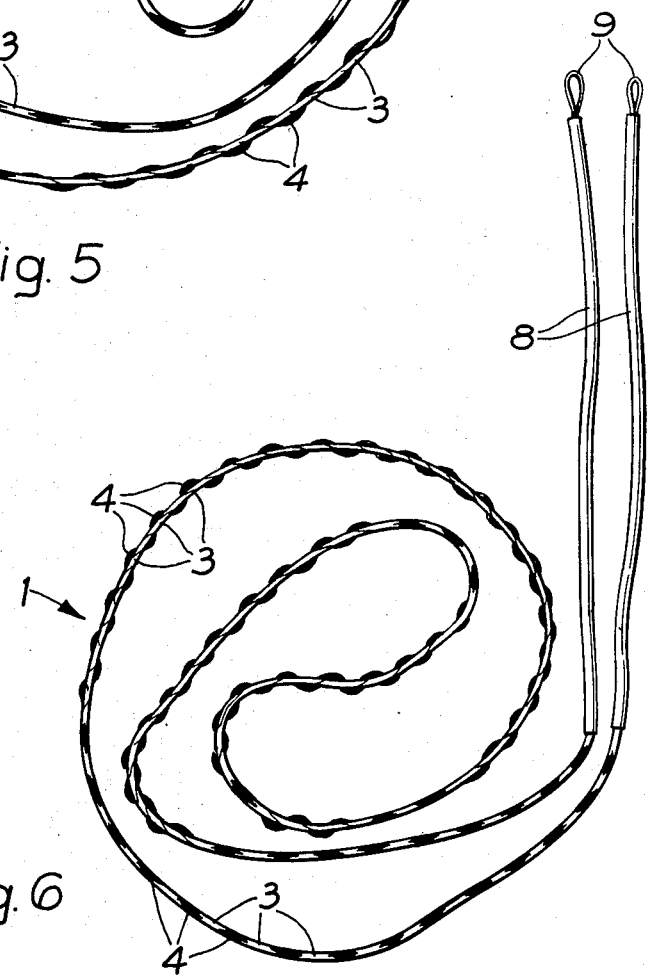

FIG. 4 corresponds to FIG. 2 but shows a core of polyester filaments as well as partial sheathing of polyester filaments;

FIG. 5 is an elevation of another surgical element in accordance with the invention, doubled up and provided with a single probe so as to serve as a tow for liagament repair;

FIG. 6 corresponds to FIG. 5 but shows an embodiment having a probe at both ends of a single length element;

FIG. 7 is an elevation of a further embodiment consisting of a surgical element in acccordance with the invention doubled up many times to form a synthetic ligament replacement having a loop at both ends for anchoring devices; and FIG. 8 shows typical load/extension curves for two carbon fibre core/polyester sheathing embodiments of the invention.

Figure 1:
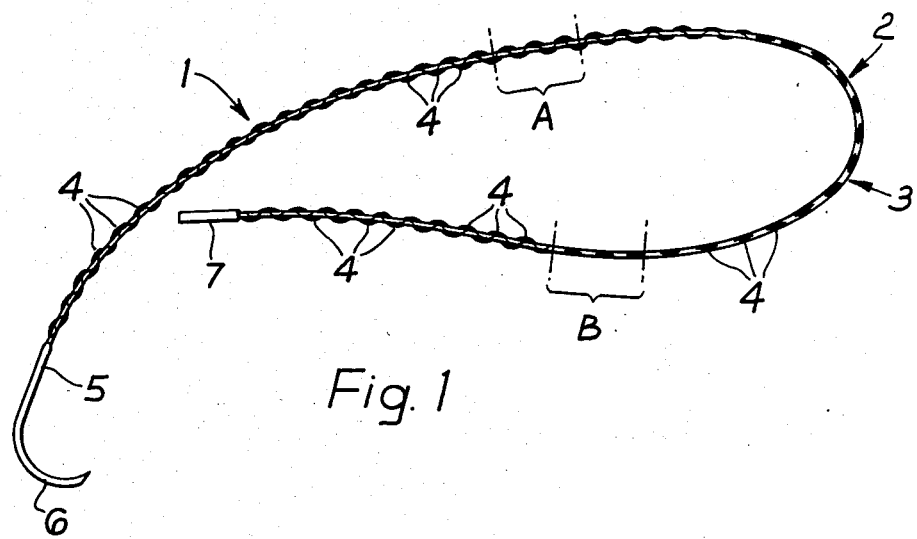
FIG. 1 is an elevation of a surgical element in accordance with the invention, having a core of carbon fibres and partial sheathing of polyester filaments, and provided with a needle so as to serve as a light duty suture.
Figure 3:
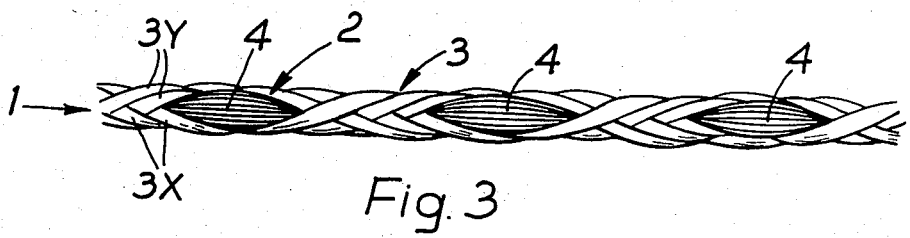
FIG. 3 is an enlargement of a portion 'B' of the surgical element shown in FIG. 1 and lying orthogonally with respect to the portion 'A'.

In FIGS. 1 to 3, a surgical element 1 comprises a core 2 consisting of a multiplicity of carbon fibres and partrial sheathing 3 formed of polyester filaments distributed in at least two groups 3X, 3Y of a width such that the aggregate of their widths is less than the circumference of the core, the groups of sheathing filaments being interwoven with contra-rotation about the core so that areas 4 of the carbon fibre core are exposed at frequent intervals along the length of the element, to encourage penetration and ingrowth of fresh tissue between the carbon fibres.

The surgical element is conveniently formed in a braiding machine, not shown but one example of which is known universally as the "J. B. Hyde Pickmaster", in which a number of bobbins are not utilised and in which two equal sets of contra-rotating bobbins are utilised. The carbon fibre core 2 is under negligible tension during the weaving of the sheathing filaments 3, so that the carbon fibres in the exposed areas 4 tend to bulge and sep rate slightly, thus further encouraging penetration and ingrowth of fresh tissue, and—because the two equal sets of contra-rotating bobbins results in two equal groups of sheathing filaments 3X, 3Y being interwoven—the exposed areas 4 of carbon fibres alternate from side-to-side of the element 1, giving a sinusoidal or distinctive 'zigzag' appearance to the element.

In FIG. 4 the core 2 is formed of polyester filaments—otherwise the surgical element 1 is of similar form to that of FIGS. 1 to 3, but also has a closer weave of the groups 3X, 3Y of the sheathing filaments, giving rise to a closer spacing of the exposed areas 4 of the core filaments.

In FIG. 1 the surgical element 1 is secured at one end in the shank 5 of an arcuate needle 6, for use of the element as a suture, and the other end is sheathed with plastics material 7 to prevent it unravelling.

In FIG. 5 a ligament repair tow consists of the surgical element 1 doubled up and provided with a single probe 8, formed by a plastics sheath over the two ends of the element, and with a looped pulling wire 9, while in FIG. 6 another ligament repair tow consists of a single length surgical element 1 with a probe 8 at both ends and each with a looped pulling wire 9.

In FIG. 7 a ligament replacement prosthesis consists of the surgical element 1 doubled up many times (e.g. forty times) to form a syunthetic ligament replacement having a loop 10 at both ends, (with braiding 11) to form eyes for a toggle 12 at one end and an anchoring screw 13 (with washer 14) at the other, the toggle being captive but the screw being provided separately, for use when the ligament replacement has been drawn into the required position across a joint by means of a probe 8 (with a looped pulling wire 9) uniting the ends of a tape 15 looped through the eye, the tape being cut when the screw is inserted into a hole in a bone drilled for that purpose.

A biocompatible lubricant is preferably applied to the surgical elements 1 to ease their passage through tissue and/or bone during the operative procedure.

When a surgical element 1 in accordance with the invention, formed with the core filaments 2 under negligible tension during the weaving of the sheathing filaments 3, is placed under tension the sheathing filaments will take the initial strain, as illustrated by the portions 16 of the load/extension curves in FIG. 8 relating to two ligament repair tows LRT 1 and LRT 2, respective details of which are given in the following table:

|  | LRT1 | LRT2 |
| --- | --- | --- |
| Number of carbon fibres in core | 12,000 | 24,000 |
| Denier of polyester sheathing filaments | 6,000 | 12,000 |
| Ultimate Tensile Strength | 500 N | 1200 N |
| Extension at failure of core fibres | 9.5% | 9.5% |
| Extension at failure of sheathing filaments | 15.0% | 12.0% |

When the extension of the sheathing filaments 3 equals the predetermined slack in the core filaments 2, as indicated by the steps 17 in the curves in FIG. 8, the core filaments will thereafter also take strain, as illustrated by the portions 18 of the curves.

What we claim is:

1. A surgical element comprising a core consisting of a multiplicity of flexible filaments and partial sheathing therefor formed of filaments of at least one standard implantable grade polymer distributed in at least two groups of a width such that the aggregate of their widths is less than the circumference of the core, the groups of sheathing filaments being interwoven with contra-rotation about the core so that areas of the core filaments are exposed at frequent intervals along the length of the element so as to promote penetration and ingrowth of tissue between the core filaments.

2. A surgical element as in claim 1, wherein the core filaments are fine carbon fibres.

3. A surgical element as in claim 1, wherein the core filaments are formed of biocompatible or bioreactive polymer.

4. A surgical element as in claim 1 wherein the polymer is a polyester.

5. A surgical element as in claim 1, formed by doubling up said surgical element with at least one loop positioned at least at one end forming an eye for use in securing to bone by means of an attachment device engaging with the eye for use as a prosthesis or replacement element for a ligament or tendon.

6. A surgical element as in claim 1 coated with a biocompatible lubricant.

7. A surgical element as in claim 1, wherein the core filaments are provided under negligible tension during weaving of the sheathing filaments sufficient to cause the core filaments in the exposed areas to bulge and separate slightly.

8. A surgical element as in claim 1, wherein two equal groups of sheathing filaments are incorporated and interwoven to provide the exposed areas of core filaments to alternate from side-to-side of the element.

9. A surgical element as in claim 1, said surgical element being doubled up on itself.

* * * * *